United States Patent [19]

Bell et al.

[11] 4,113,832

[45] Sep. 12, 1978

[54] PROCESS FOR THE UTILIZATION OF WASTE MATERIALS FROM ELECTROLYTIC ALUMINUM REDUCTION SYSTEMS

[75] Inventors: Norman Bell, Livermore; John N. Andersen, Moraga; Hung-Kei H. Lam, Walnut Creek, Ala.L OF CA

[73] Assignee: Kaiser Aluminum & Chemical Corporation, Oakland, Calif.

[21] Appl. No.: 855,506

[22] Filed: Nov. 28, 1977

[51] Int. Cl.² ........................... C01F 7/04; C01B 7/19
[52] U.S. Cl. ..................................... 423/119; 204/67; 423/111; 423/133; 423/131; 423/240; 423/484; 423/489; 423/179; 423/200
[58] Field of Search ............... 423/111, 119, 133, 240, 423/489, 484; 204/67

[56] References Cited

U.S. PATENT DOCUMENTS

| | | | |
|---|---|---|---|
| 3,151,934 | 10/1964 | King | 423/179.5 |
| 3,606,176 | 9/1971 | Vodic | 241/24 |
| 3,635,408 | 1/1972 | Williams | 204/294 |
| 3,780,497 | 12/1973 | Muhlrad | 423/240 |
| 3,907,971 | 9/1975 | Bohm et al. | 423/240 |
| 4,006,066 | 1/1977 | Sparwald | 204/67 |
| 4,053,375 | 10/1977 | Roberts et al. | 204/67 |
| 4,062,696 | 12/1977 | Ducote | 204/67 |

Primary Examiner—Herbert T. Carter
Attorney, Agent, or Firm—Paul E. Calrow; Andrew E. Barlay

[57] ABSTRACT

A fully integrated process is provided for the recovery of valuable components from waste materials generated in electrolytic aluminum reduction systems. The waste materials, such as spent pot linings, channel and trench cleanings, floor sweepings and spent alumina from off-gas purifying dry scrubbers, are combined, then pyrohydrolyzed at elevated temperature. Fluoridic values, such as NaF and HF can be recovered from the offgas generated by pyrohydrolysis, while alumina and $Na_2O$ values, or if desired, sodium aluminate, is reclaimed from the solid residue of pyrohydrolysis.

The fluoridic values from the pyrohydrolysis offgas can be used for the manufacture of both electrolytes for aluminum reduction cells and also for the production of anhydrous HF. The alumina from the pyrohydrolysis residue can be reclaimed by a Bayer process-type leach with a caustic solution and the recovered high purity alumina utilized, for example, as reduction cell feed and/or for scrubbing reduction cell offgases. If the solid residue of pyrohydrolysis contains significant amounts of sodium aluminate, this material can either be directly used for dry scrubbing cell offgases, or if desired, utilized for production of high purity alumina.

15 Claims, 1 Drawing Figure

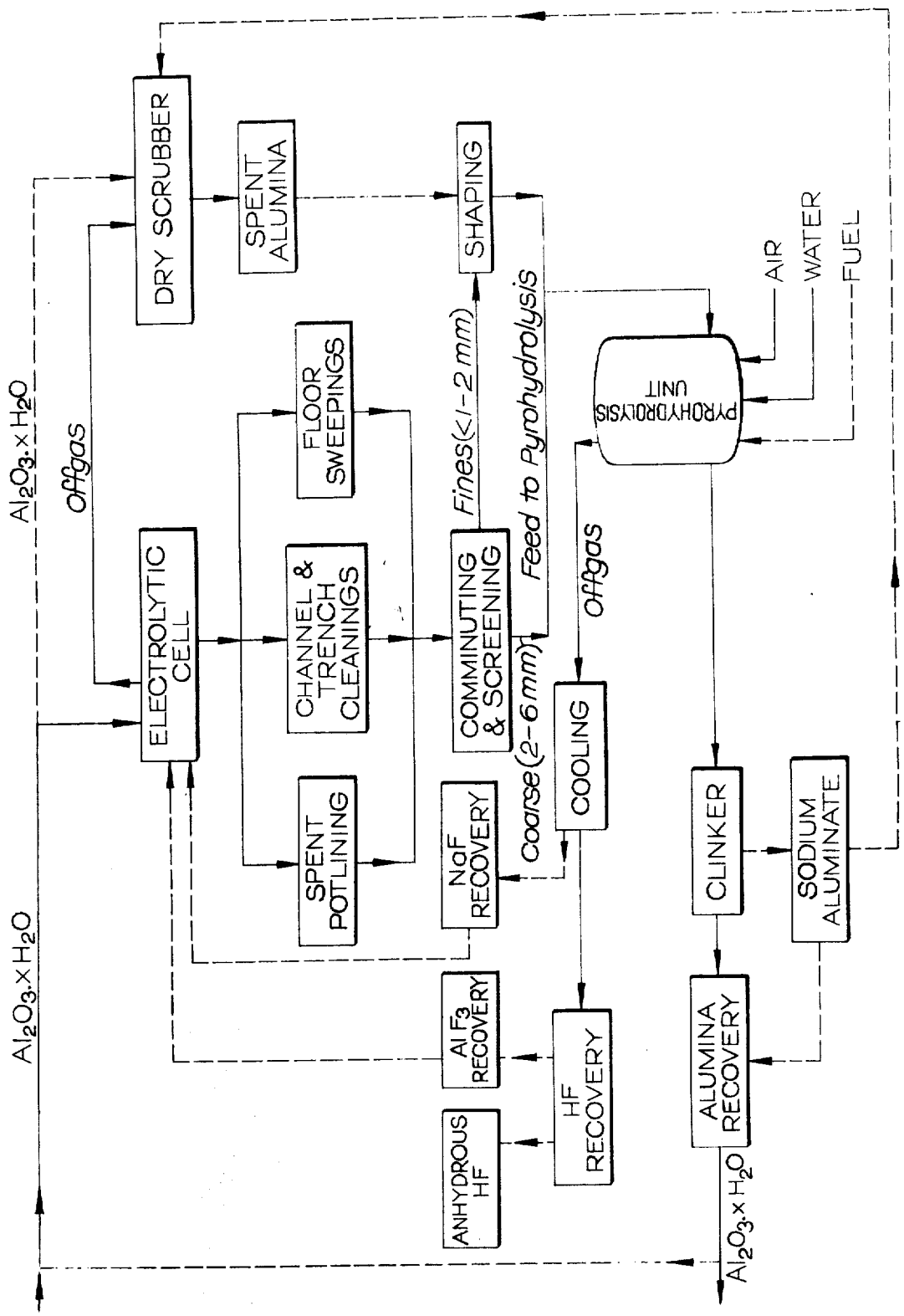

PROCESS FOR THE UTILIZATION OF WASTE MATERIALS FROM ELECTROLYTIC ALUMINUM REDUCTION SYSTEMS

BACKGROUND OF THE INVENTION

This invention relates to a fully integrated system for the recovery of valuable components from spent materials generated in the electrolytic reduction of alumina to metallic aluminum with simultaneous improvement in the purity of aluminum produced in the reduction process.

In the production of metallic aluminum by electrolysis of reduction-grade $Al_2O_3$, the electrolysis is generally carried out in reduction cells or pot lines which are lined with a carbonaceous material. During the life of the cells, this carbon lining is gradually destroyed by penetration of bath materials into the lining, for example, metallic aluminum, cryolite and alumina. Also, due to the high temperatures employed in the electrolytic reduction process, gradual aging of the carbonaceous lining takes place. The combined result of penetration and aging can reach a stage where the further operation of the cell or cells reaches an economically prohibitive point and replacement of the carbonaceous lining becomes a must. The unusable or "spent" potlining is then removed and in most instances stockpiled. In large aluminum reduction facilities, this lining replacement is a continuous process and, consequently, the quantity of spent lining stockpiled increases from day to day.

In aluminum reduction facilities, where metallic aluminum is produced by the electrolysis of $Al_2O_3$ in the presence of a fluoridic electrolyte, such as cryolite ($Na_3AlF_6$), the electrolysis results in offgases of high fluoride content. In addition to the fluoride content, the offgases generated in the reduction process contain gaseous and particulate impurities, for example, volatilized metallic compounds and carbon derivatives, together with solid matter and nonvolatile carbonaceous materials. The quantity of volatilized and solid carbon compounds in the offgases vary within wide limits depending on the type of anode used in the reduction system. Soderberg carbon anodes generate far more of these materials than prebaked carbon anodes.

In order to protect the environment and to provide healthy operating conditions in the reduction facility, these offgases must undergo a purification process for the removal of harmful constituents. A common process for cleaning the offgases is to subject them to a dry scrubbing treatment which effectively removes essentially all of the environmentally harmful impurities from the offgases. In the dry scrubbing treatment of reduction offgases, alumina is usually employed as the scrubbing medium. The alumina readily absorbs the fluoridic components of the offgases and also captures the particulate impurities. It further removes harmful high molecular weight carbon derivatives. Consequently, the dry scrubbing of reduction cell offgases with alumina is an effective purification process resulting in purified offgases containing only environmentally harmless components.

While scrubbing of the offgases solves the environmental and health problems, it poses a serious disposal problem. The spent alumina from the scrubber system is heavily laden with impurities and cannot be directly employed as feed for reduction cells without introducing unacceptable alloying components in the metal to be produced and without seriously interfering with the efficient operation of the reduction cells. Since the alumina is spent, it cannot be used for further scrubbing without purification.

In the production of metallic aluminum by the electrolytic reduction of $Al_2O_3$ in a series of cells, a significant quantity of impure metal and contaminated aluminum oxide feed are also generated in the form of floor sweepings, channel and trench cleanings. These materials, due to their high impurity content, cannot be directly employed for making metallic aluminum of commercial purity and, in general, if not blended with pure feed materials, are considered as waste with no convenient way of disposal.

Thus, from the above, it becomes clear that the producers of aluminum by the electrolytic process have major problems relative to the disposal of spent potlinings, exhausted alumina from the dry scrubbers, floor sweepings, channel and trench cleanings. These problems have been acutely recognized by operators of aluminum reduction facilities all over the world and partial solutions have been offered to overcome one or more of the problems associated with the generation of these spent materials.

Several proposals have already been made to deal with the problems resulting from the accumulation of excessively large quantities of spent potlinings.

Thus, in U.S. Pat. No. 3,151,934, it has been suggested that the spent potlinings be crushed, followed by extraction of fluoridic values and dissolution of metallic aluminum with a sodium hydroxide solution. The alkaline extract, after carbonation, is utilized for the preparation of synthetic cryolite, while the essentially fluoride-free carbon residue, is again contacted with an $NaOH-Ca(OH)_2$ solution. This treatment of the carbon residue or "black mud" removes any lithium present and then the black mud residue is disposed of. The treatment disclosed in this reference results in only a partial and expensive solution of the disposal problem; large quantities of black mud remain after the extraction treatments which cannot be utilized for any forseeable purpose.

In U.S. Pat. No. 3,606,176, it has been suggested to crush the spent lining of reduction cells, followed by removal of the metallic aluminium content by mechanical screening. The residual crushed carbonaceous lining is then further reduced in size and subsequently slurried with salt water to allow separation of the bulk of the carbon fraction by flotation from cryolite, alumina and residual aluminum. Again, the carbon fraction is discarded and since this is the major portion of the spent lining, stockpiling with the corresponding problems has not been solved.

Another process for treating spent potlinings is presented in U.S. Pat. No. 3,635,408. According to this reference, spent carbon lining is crushed, then treated with dry steam at a temperature insufficient to destroy the carbon. The steamed, carbonaceous material is then classified into coarse and fine fractions. The fine fraction is subjected to a chemical treatment for the recovery of its fluoridic values, together with the alumina and aluminum content, while the coarse fraction is utilizable for making new cell linings. However, if the coarse fraction resulted from cell linings of the monolithic type, the coarse fraction has an approximate carbon content of only 53%, the balance being fluorides, alumina and aluminum. This relatively high percentage of impurity content, when the coarse fraction is used directly for making of new cell linings, will adversely affect the electrical and mechanical properties of the new cell lining and, consequently, will provide lower life expectancy, coupled with operating efficiencies below the desired parameters. If the coarse fraction results from spent linings made of the prebake type, the carbon content is higher and the undesirable impurity content is lower. However, the new linings made from this material will still perform below the desired values in terms of efficiency and life.

Thus, it can be observed that although many efforts have been made to utilize the spent linings of reduction cells, these efforts only provided partial solutions to the existing problems which the ever-increasing piles of spent potlinings further emphasize.

Regarding the spent alumina recovered from the dry scrubber systems, several processes have already been recommended for the treatment of this impurity-laden material. For example, German Pat. No. 970,919 (granted Nov. 13, 1958) has recommended the calcination of the spent alumina removed from the scrubber system. Calcination of this alumina in the presence of sodium carbonate below the sintering temperature of cryolite results in cryolite which can be recycled to the reduction cells as electrolyte. This cryolite would be a suitable substitute for either natural or synthetic cryolite generally employed for this purpose if it would be free of metallic impurities. However, the calcination employed to convert the spent alumina to cryolite can only remove some of the volatilizable impurities and perhaps carbon. It does not eliminate the metallic impurities, such as iron, silicon and phosphorus, and, consequently, by recycling it directly to the cell, the undesired impurity content in the produced metallic aluminum will constantly increase. This increase in impurity level significantly lowers the commercial value of the produced aluminum, apart from the deleterious effects caused by these impurities with regard to the cell lining life and efficiency of the electrolytic reduction process.

More currently, it has been suggested in U.S. Pat. No. 4,006,066, that the spent alumina from dry scrubbers, which are appended to the electrolytic aluminum reduction cell system, can be purified by classifying the impurity-laden alumina to coarse and fine particle size fractions. The reason for this size separation is the fact that the major quantity of impurity from the reduction cell offgas is captured by the fine fraction of the alumina employed in the scrubber system. The coarse fraction will also capture impurities from the offgas; however, the impurity content of the coarse fraction is significantly smaller in proportion to its weight. Consequently, separation by size affords a preliminary purification and allows the return of the coarse fraction directly to the reduction cell as partial feed and also as partial fluoridic electrolyte replacement. This recycling of the coarse fraction, which can amount to up to about 80-85% of the alumina from the scrubber system, greatly assists in reducing the quantity of alumina to be purified before further utilization. The impurity content of this coarse fraction nevertheless still causes similar problems as described hereinbefore.

The fine fraction from the classification contains the major amount of the impurities from the reduction cell offgases and this fraction, while smaller in percentage by weight than the coarse fraction, still presents a large quantity to be dealt with. The aforesaid U.S. reference pyrohydrolyzes this fine fraction in a special rotary kiln with water vapor and the resulting alumina product, which is free of fluorine, but still contains the other impurities as stated, is usable, for example, in the ceramic industry. This alumina, due to its high impurity content, cannot be returned to the electrolytic aluminum production system. Consequently, it constitutes a significant loss and affects the overall economy of aluminum production.

Even more recently, in copending U.S. pat. application Ser. No. 709,025 (filed July 27, 1976), a process has been described which allows the separation of essentially all of the impurities from the spent alumina recovered from the dry scrubbers of aluminum reduction cell offgases. This is accomplished by slurrying the spent alumina with a solvent, followed by an ultrasonic treatment of the slurry. Although the ultrasonically treated, highly pure alumina can be recycled to the scrubber system or the cells after drying, the process, due to the large quantities of spent alumina to be treated, can create logistics problems and equipment constraints.

Channel and trench cleanings and floor sweepings found in aluminum reduction facilities can contain a large percentage of metallic aluminum, together with cryolitic flux and aluminum oxide. Recovery of the aluminum values can be accomplished by screening or melting these materials in a furnace in the presence of a suitable flux. This operation requires special equipment and chemicals, not to mention the significant input of energy. This type of purification allows the recovery of metallic aluminum; however, both the cryolite and the alumina values become lost and in addition, the process poses disposal problems.

From the above, it can be observed that there is a need for an integrated system which is capable of dealing with all of these spent materials with simultaneous recovery of all of the valuable components from these by-products of the electrolytic aluminum reduction process. The integrated system described hereinafter provides such a solution whereby all of the above-described spent materials can be fully utilized without affecting the purity of the metallic aluminum produced in the electrolytic reduction cells.

BRIEF SUMMARY OF THE INVENTION

An integrated process is provided for the recovery of valuable components from aluminum, carbon and fluoride-containing waste materials generated in electrolytic aluminum reduction systems. From these waste materials, which include spent potlining, spent alumina from dry scrubbers used for reduction cell offgas purification, channel and trench cleanings and floor sweepings, a feed is prepared for a pyrohydrolysis unit. Preparation may include comminution to less than about 6 mm particle size if the waste material is of greater size. If there are fine particles below about 1-2 mm in size, these are advantageously shaped prior to pyrohydrolysis. Also, if desired, sufficient carbon can be added to the feed to provide self-sustaining combustion in the pyrohydrolysis unit. Pyrohydrolysis of the feed is accomplished at about 1100° to 1350° C., while sufficient water is introduced into the pyrohydrolysis unit to obtain an offgas containing the fluoridic values from the feed. The offgas, after cooling, may be sequentially utilized for the production of NaF or an NaF-enriched alumina in controlled amount. Then either an $AlF_3$-enriched alumina or an HF solution is made. The solid clinker resulting from pyrohydrolysis is utilized for the production of high purity alumina and recovery of $Na_2O$ values by treating it according to the Bayer process. If desired, sufficient basic sodium salts, such as $Na_2CO_3$ and/or NaOH, is added to the feed or the hot clinker. In this instance, the clinker recovered from the pyrohydrolysis unit will contain a major amount of sodium aluminate. This sodium aluminate can either be used for the production of alumina or employed in dry scrubbers for the capture of impurities emanating from reduction cells. If desired, the sodium aluminate can be used for both of these purposes.

BRIEF DESCRIPTION OF THE FIGURE

The FIGURE provides a schematic flowsheet for the recovery of valuable components from waste materials generated in electrolytic aluminum reduction systems. Dotted lines indicate optional process steps.

DETAILED DESCRIPTION OF THE INVENTION

The present invention relates to an integrated system for the recovery of valuable components of spent materials generated in electrolytic aluminum reduction facilities. More particularly, it concerns a fully integrated process which allows recovery of essentially all of the alumina, fluoride and alkali values from spent potlinings, spent alumina from dry scrubbers, channel and trench cleanings and floor sweepings of electrolytic aluminum reduction plants.

In the instant process, the spent materials are first formed into an easily fluidizable form, then this material is subjected to pyrohydrolysis. Pyrohydrolysis will remove essentially all of the combustible matter and volatilizable fluoride content of the material. The pyrohydrolysis residue will consist of a clinker-type material containing all of the noncombustible and nonvolatilizable matter, together with the alumina and the oxidized aluminum content of the spent materials. Alkaline extraction of the clinker results in the generation of an alkali aluminate solution and an insoluble residue containing essentially all of the other nonsoluble content of the spent materials. The alkaline aluminate solution can be utilized for the production of high purity hydrated alumina, which, after a thermal treatment, can either be used as feed for the reduction cell and/or as dry scrubbing medium; or, for example, for catalyst or catalyst supports.

The valuable volatiles generated in the pyrohydrolysis step are also fully utilized. For example, the offgases resulting during pyrohydrolysis, after removal of the coarse entrained solids content, contain a substantial quantity of fluoridic material, such as HF and NaF. The HF can be readily used in the manufacture of aluminum fluoride, cryolite or anhydrous HF; or for all of these purposes, while the NaF can be recovered as such in varying concentration. The individual process steps of the instant integrated system will be shown in detail below:

I. Characterization of Spent Materials from Electrolytic Aluminum Reduction Facilities

(a) Spent Potlining

Almost all spent potlinings obtained from the electrolytic aluminum reduction cells contain in addition to the major component of carbonaceous material, a significant quantity of noncarbonaceous matter. The noncarbonaceous content can vary within wide limits, depending upon the operating conditions of the pot, the type of electrolyte employed and the age of the lining. The composition of a typical spent potlining is given in Table I.

Table I

| Composition of Typical Spent Potlining | | | |
|---|---|---|---|
| Elements | % by Weight | Elements | % by Weight |
| Al | 16.1 | Ca | 1.4 |
| F | 10.5 | Fe | 0.8 |
| Na | 11.8 | Si | 0.7 |
| Li | 0.3 | CN | 0.2 |
| C | 32.1 | $O_2 + CO_3 + Cl$, etc. | 26.1 |

(b) Spent Alumina from Dry Scrubbers

In the purification of electrolytic aluminum reduction cell offgases for the capture of fluoridic impurities, alumina of the general formula $Al_2O_3 \cdot xH_2O$ is commonly employed. The value of $x$ in these aluminas varies within the limits of about 0.05 to 3, the value 3 denoting the fully hydrated alumina, i.e., $Al_2O_3 \cdot 3H_2O$. Aluminas having an $x$ value of less than about 0.05 are rarely employed, since the active surface of these aluminas is small and capture of fluoridic values by $Al_2O_3 \cdot 0.05\ H_2O$ is relatively low. For optimum fluorine removal from the reduction cell offgases, aluminas having an active surface area between about 20 $m^2/g$ and 400 $m^2/g$ are utilized. The type and quantity of impurities captured by the alumina of the dry scrubber systems vary within wide limits, depending upon the operating conditions of the cells. Also, it is affected by the type of anodes employed in the cell, the composition of the fluoridic electrolyte utilized in the reduction of alumina and also on the impurity content of the alumina charged as feed to the cells and also to the dry scrubbers.

Consequently, the impurity content of the spent alumina from the dry scrubbers depends on many factors and cannot be accurately defined. In Table II below, the composition of a spent alumina charge from a dry scrubber is given. The offgases emanating from cells equipped with Soderberg electrodes generate significant quantitites of carbonaceous impurities both in volatilized and in particulate form. The spent alumina charge, which is shown in Table II, has been removed from the dry scrubber system, when it has failed to efficiently capture additional fluoridic values from the offgas.

Table II

| Impurity Level of Spent Alumina from a Dry Scrubber System | | | |
|---|---|---|---|
| Element | % by Weight | Element | % by Weight |
| F | 3.0 | Ca | 0.058 |
| C | 1.70 | Zn | 0.002 |
| Fe | 0.94 | Mn | <0.002 |
| Si | 0.14 | Ti | 0.002 |
| Cu | <0.01 | Ga | 0.013 |
| Mg | 0.009 | Cr | <0.001 |
| Ni | 0.019 | Na | 0.66 |
| V | 0.005 | $P_2O_5$ | 0.012 |

From Table II it can be observed that the major foreign matter content in the spent alumina is constituted by F, C, Fe, Si and Na. Recycling of this impure alumina to the reduction cell would not only interfere with the operation of the cell, but would also result in aluminum enriched in metallic impurities.

(c) Channel and Trench Cleanings and Floor Sweepings

Channel and trench cleanings and/or floor sweepings vary from reduction plant to reduction plant and also from potline to potline. Consequently, it is not possible to provide an exact composition for these materials. Nevertheless, it is known that the major constituent of these "spent materials" or "waste matter" is a mixture of fluoridic materials with iron and some alumina. Thus, as it can be observed from Table III, which denotes an average composition of the major impurities in channel and trench cleanings and floor sweepings collected in a stockpile, this "waste matter" contains valuable components worth of utilization.

Table III

Average Composition of Major Impurities in Stockpiled Mixture of Channel and Trench Cleanings and Floor Sweepings

| Element | % in Weight |
|---------|-------------|
| Al | 35.0 |
| F | 25.5 |
| Na | 13.5 |
| Fe | 1.0 |
| Si | 0.4 |
| Others | Balance |

II. Preparation of Spent Material Feed to Pyrohydrolysis

(a) Comminution

Since the "spent" or "waste" materials to be treated in accordance with the invention come in all sizes, it is of the essence to obtain a particle size distribution which allows the utilization of these materials without difficulty.

Thus, spent potlining, in order to render it suitable, must be subjected to a comminuting or crushing operation. This can be achieved in any suitable apparatus, for example, jaw crushers. The crushed material can then be further reduced in size, for example, to less than about 6 mm size, by use of impact mills. The size range desired for the comminuted spent potlining is within the size limits of about 2-6 mm. Comminution allows a partial segregation of metallic aluminum from the balance of the spent potlining materials; the more than 6 mm size particles remaining after crushing contain most of the metallic aluminum, which can be readily sorted out and returned to remelting pots. Naturally, this separation is optional, the metallic aluminum in the spent potlining if desired can be readily converted to alumina during the pyrohydrolysis treatment, thus rendering the separation superfluous.

Channel cleanings, trench cleanings and floor sweepings also come in diverse particle sizes and to obtain a particle size which will enable further processing, it may also be necessary to subject this type of waste material to a comminuting step.

With regard to the spent alumina from the dry scrubber system, generally no comminution or grinding is required. The alumina employed in the scrubbers has usually a particle size below about 5 mm, generally less than about 1 mm. Consequently, unless aggregates form during dry scrubbing of reduction cell offgases, no size reduction is required.

(b) Shaping (Optional)

In order to obtain optimum efficiency in the reclaiming of valuable components from the spent materials, it is recommended to shape any of the matter having a particle size below about 1-2 mm. Suitable shapes include pellets, granules, briquettes and other forms of aggregates, such as extrudates, which allow easy transfer of the materials to the pyrohydrolysis unit, ready fluidization, as well as trouble-free stockpiling of the shaped materials without excessive dust formation.

The carbon content of spent potlinings is normally sufficient to provide enough fuel value for the pyrohydrolysis step contemplated. However, if the shaped material contains significant quantities of noncarbonaceous waste matter, e.g., spent alumina from the dry scrubbers, it is considered advisable to incorporate additional carbon in the mixture to be shaped. This improves the overall heat balance of the reclaimining process of the present invention and additionally assist the pyrohydrolysis step.

III. Pyrohydrolysis

(a) Equipment

Pyrohydrolysis of the waste material can be readily accomplished in any type of equipment capable of providing good gas to solids contact, such as a fluid bed. Generally, a refractorylined furnace is employed to protect the walls of the furnace against the erosive and corrosive effects of the charge, particularly under the pyrohydrolysis conditions present in the furnace and the elevated temperature. The furnace employed for the pyrodrolysis can also be an expanded bed furnace, such as is known in the art. Depending upon the quantity of spent material to be pyrohydrolyzed, one or more units can be employed.

The term "pyrohydrolysis" for the pusposes of the instant invention refers to the reaction of fluoridic materials with water at elevated temperature according to the reaction shown below:

$$2NaF + H_2O \rightleftarrows Na_2O + 2HF \quad (1)$$

Under conditions shown, the following reaction also takes place:

$$Na_2O + Al_2O_3 \rightarrow 2NaAlO_2 \quad (2)$$

Reaction (1) is an equilibrium reaction and one may shift it towards the production of HF by supplying sufficient $Al_2O_3$ to the pyrohydrolysis unit, which will combine with the $Na_2O$ to form sodium aluminate. Thus, one may control the amount of HF and/or NaF in the pyrohydrolysis offgases by varying the quantity of $Al_2O_3$ in the unit.

(b) Operation of the Pyrohydrolysis Unit

The temperature in the pyrohydrolysis unit is maintained at such a level as to allow combustion of the carbonaceous matter content of the charge. In order to start up the unit, the necessary heat for establishing fluidized bed conditions can be obtained either by direct firing or by indirect means. It has been found that in order to achieve both carbon combustion and pyrohydrolysis of the fluoridic components of the charge, the temperature in the pyrohydrolysis unit should be kept at least about 1100° C. For optimum operating results, the temperature in the pyrohydrolysis unit is generally kept within the range of about 1150°-1250° C. Pyrohydrolysis of the charge is carried out by wellknown techniques using sufficient moisture to provide for the desired hydrolysis. This moisture can be either introduced as liquid, vapor or the charge can be prewetted. Combinations of these can be equally utilized.

IV. Recovery of Valuable Components from Spent Materials Recovery of Volatiles As a result of the pyrohydrolysis under the conditions described above, the fluoride content of the spent material charge to the pyrohydrolysis unit will be volatilized. The main components of the volatile or vaporized stream which are discharged from the pyrohydrolysis unit consist of hydrogen fluoride and sodium fluoride. Since the vaporized materials exiting from the pyrohydrolysis unit are at elevated temperature, it is necessary to cool these vapors.

Cooling of these vapors can be accomplished in any suitable apparatus capable of removing a substantial quantity of the heat from the vapors. The type of cooling equipment and/or cooling medium utilized can also influence the nature of the recovered fluoridic materials. Thus, for example, if the hot vapors are contacted with a water spray in a cooling tower, and the vapors are cooled below the dew point of the gases, an aqueous HF solution is recovered. The concentration of HF in this solution can vary within wide limits, depending upon the quantity of HF in the vaporized material and the volume of water employed for spray cooling. Naturally, the cooling can be accomplished above the dew point of the gases.

In the event the cooling is accomplished by indirect heat exchange using a suitable exchange medium, the HF content of the gas will remain undiluted by the cooling agent and may be recovered in a higher concentration.

In an advantageous variation of the cooling step employed for decreasing the temperature of the pyrohydrolysis offgases, the hot offgas exiting from the pyrohydrolysis unit is first shock-chilled with a blast of cold gas. The partially cooled gas is then further cooled to, say about 250°-280° C., by contact with water. A portion of this cooled gas can be recycled for cooling hot offgases from the pyrohydrolysis unit, while the balance of the cooled gas is utilized for the recovery of its fluoride content. This mode of chilling results in a less diluted offgas which permits even more efficient recovery of the fluoridic values from the offgas. It is understood that, if desired, air or a mixture of air and cold offgas may also be employed for cooling.

(a) Recovery of NaF

As has been shown previously, the NaF content of the pyrohydrolysis offgas can be readily controlled by the quantity of alumina present in the pyrohydrolysis unit. Thus, if generation of an offgas, containing no significant amounts of NaF, is desired, the $Al_2O_3$ content of the pyrohydrolysis feed is upwardly adjusted to provide at least a stoichiometric $Na_2O$ to $Al_2O_3$ ratio. The reaction between these reactants shifts the pyrohydrolysis equation (1) to the right, resulting in the formation of HF with elimination of NaF production in the offgas. If, however, generation of NaF is aimed at, the $Al_2O_3$ content of the pyrohydrolysis feed is not adjusted or is only increased to such a level where a desired quantity of NaF is produced.

When it is desired to produce NaF in the pyrohydrolysis process, the offgass will contain the NaF in a very finely divided form, such as a fume. Collection of these fine particles is difficult and even when collection is successfully achieved, further handling of these fine particles involve several problems including dusting. It has been found that these problems can be readily overcome by providing a fluidized alumina bed which acts as an absorber and "filter" for these fine NaF particles. In the fluidized alumina bed, a mixture of NaF—$Al_2O_3$ is produced and the fluidized bed can also act as an absorber for other fluoridic compounds, such as LiF and/or $CaF_2$, which are often found in the spent materials of reduction cells. In Table IV, a typical composition of the product recovered from a fluidized alumina bed intended to capture the fine fluoridic particles generated during pyrohydrolysis is shown.

Table IV

Typical Composition of Product Recovered from Fluidized Alumina-Sorption Unit

| Constituent | % by Weight |
|---|---|
| $Al_2O_3$ | 44.4 |
| NaF | 44.8 |
| $AlF_3$ | 7.2 |
| $CaF_2$ | 0.1 |
| LiF* | 3.0 |
| Others | 0.5 |

*Only present if electrolyte feed to aluminum reduction cell contained LiF as a component Although this product does not contain cryolite ($Na_3AlF_6$) as such, the composition of the mixture as far as distribution of the important elements is concerned allows it to be directly employed as electrolyte for aluminum reduction cells. If desired, the fluoridic alumina produced in the fluidized bed sorption unit can be shaped, for example, pelletized, this improves the handling of this material, as well as provides essentially dustless conditions when this material is charged to aluminum reduction cells. Shaping can be done by any well-known technique.

(b) Recovery of HF

Depending upon the manner of cooling, HF in varying concentration is obtained. If the cooling of the hot gases emanating from the pyrohydrolysis unit is accomplished by the application of water spray, then the HF content of the gas, which, depending upon the F content of the spent material to the pyrohydrolysis, is in the range of 1% to 2% by volume, will be diluted. This diluted HF stream, due to the lowered HF content, is generally unsuitable for the preparation of anhydrous HF. Concentration of the diluted stream to an HF content above that of the azeotropic composition is expensive and involved; consequently, the stream is rather employed for the preparation of aluminum fluoride ($AlF_3$). This is conveniently accomplished by contacting the stream of dilute HF with a fluidized bed of alumina. The reaction of the HF stream with, for example, reduction-grade alumina, such as used as feed to electrolytic aluminum reduction cells, results in a mixture of aluminum fluoride and alumina. The contacting of the dilute stream with the fluidized alumina bed is conducted until a mixture of about 10 to 15% $AlF_3$ content is obtained. It has been observed that as a result of the relatively low HF content of the stream, as indicated above, equilibrium conditions arise with no further increase in the $AlF_3$ content in the fluidized bed. Naturally, if the stream is more concentrated in HF than shown above, equilibrium conditions or break-through in alumina conversion capability occurs at higher $AlF_3$ concentration levels. In lieu of a single bed, multiple fluidized alumina beds can be employed.

The $AlF_3$-alumina product obtained in the HF sorption step can be directly employed as feed to the aluminum reduction cells where the $AlF_3$ content of the material will act as electrolyte, together with the NaF-alumina product from the NaF sorption stage.

In the event the cooling of the HF-containing stream from the pyrohydrolysis unit is accomplished, for example, by indirect heat exchange, the HF content of the stream remains undiluted. This stream, which does not contain extraneously introduced water vapor, has a relatively high HF content which allows the processing of this stream for making highly concentrated HF and ultimately anhydrous HF. Thus, this HF-containing stream can be readily utilized either for the preparation of fluoridic bath chemicals, such as $AlF_3$, cryolite; or, if desired, employed for making anhydrous HF which is an important source of fluorine for many chemicals. Conversion of the HF to the anhydrous acid can be accomplished by preliminary concentration, for example, by distillation, followed by preparation of an organic-fluorine complex according to the prior art from which anhydrous HF can be recovered by known techniques.

V. Recovery of Valuable Components from the Clinker Produced in the Pyrohydrolysis Unit Pyrohydrolysis of the spent materials described above results in a clinker. This clinker contains aluminum oxide and $Na_2O$ as its major component and as minor constituents, the metallic impurities present in the spent materials subjected to pyrohydrolysis. As mentioned hereinbefore, the metallic Al content, which has not been removed by physical segregation prior to hydrolysis, converts to $Al_2O_3$ under the conditions of pyrohydrolysis. A typical clinker composition, resulting from the pyrohydrolysis of a spent potlining charge, is shown in Table V.

Table V

| Typical Clinker Composition from Pyrohydrolyzed Spent Potlining | |
|---|---|
| Composition | % by Weight |
| $Al_2O_3$ | 64.0 |
| $Na_2O$ | 28.0 |
| F | 1.0 |
| CaO | 2.0 |
| $Fe_2O_3$ | 2.0 |
| Others (as oxides, chlorides, etc.) | 3.0 |

Thus, it can be observed that the clinker produced by pyrohydrolysis of spent potlining results in a material which can be readily utilized for the recovery of alumina and sodium values, particularly by the Bayer process.

When the clinker, such as the above, is contacted with an alkaline solution and digested at temperatures in excess of about 200° C., preferably within the range of about 215°–250° C., substantially all of its alumina content is recovered as sodium aluminate with nearly complete rejection of the other metallic impurities present in the clinker which remain insoluble. From the sodium aluminate liquor, the dissolved alumina content is recovered by precipitation of hydrated alumina, which, when calcined at elevated temperatures, provides a high purity, reduction-grade alumina. This alumina can be readily utilized as feed for the electrolytic aluminum reduction cells or if desired can be employed in the fluidized alumina bed for capture of NaF and/or reaction with HF, as shown above.

In a variation of the instant process, the feed to pyrohydrolysis, can be combined with an alkaline material, such as sodium carbonate and/or sodium hydroxide. The quantity of alkaline agent added to the spent matter is established by the combined alumina and aluminum content of the spent material and is generally an amount at least sufficient to convert all of the aluminum and nonfluoridic alumina to sodium aluminate. The alkaline agent can be added to the comminuted spent materials in solid form, or if desired, sprayed on the material from an aqueous solution. If shaping precedes pyrohydrolysis, the alkaline agent can be added during shaping, or the shaped spent materials can be sprayed with the alkaline agent. This variant improves the recovery of alumina from the clinker by converting more of it to sodium aluminate during pyrohydrolysis.

In a further variation of the above, the hot clinker, rather than the pyrohydrolysis feed, is being contacted with the alkaline agents. Thus, according to this embodiment, the hot clinker of about 1100° C. is contacted in a soaking pit with NaOH or $Na_2CO_3$, or with mixtures of these. Contacting times of about 30 minutes or more, generally less than about 2 hours have been found sufficient to convert the alumina content of the clinker to sodium aluminate.

The alkali aluminate-containing clinker can be employed for various purposes. Thus, leaching it with water or a dilute caustic solution results in an alkali aluminate solution essentially free of metallic impurities and this solution can be employed for the production of alumina of high purity by precipitation and subsequent thermal treatment. The solid alkali aluminate clinker can also be directly utilized in dry scrubber systems for the removal of fluoridic impurities from aluminum reduction cell offgases. Due to the high fluorine capture capacity of alkali aluminates, this clinker can be readily utilized at a high degree of efficiency. Exhausted alkali aluminate from the dry scrubbers can be regenerated in the same manner as the spent alumina, i.e., by pyrohydrolysis. This embodiment completely eliminates the reintroduction of metallic impurities to the cell. Since the spent alumina from the dry scrubbers is not recycled to the cells, most of these impurities, with the exception of the fluoridic materials and carbon, remain in the alkali aluminate clinker during pyrohydrolysis. Purge of a portion of the clinker to a Bayer process-type recovery operation allows control of the impurity level of the pyrohydrolyzed clinker within desired limits and also provides disposal of excess clinker.

From the above detailed description, it can be clearly observed that the integrated process of the instant invention allows a novel, efficient, environmentally desirable and economical control of the impurities generated in the electrolytic aluminum reduction process with simultaneous recovery of substantially all of the important constituents from the spent materials.

In the following, the operation of the instant integrated recovery process is explained in greater detail. Certain of the process details and parameters shown hereinafter represent the results partially obtained in pilot plant operation and these data have been scaled up for easier comprehension to the operation of a plant capable of processing of about 30,000 tons/year spent matter generated in an aluminum reduction facility.

Example I

Recovery of valuable components from spent potlining and channel and trench cleanings, as well as floor sweepings, by the instant process is shown. The spent potlining employed in the reclamation process has been recovered from electrolytic aluminum reduction cells and its composition is shown in Table VI.

Table VI

| Composition of Spent Potlining by Elements | | | |
|---|---|---|---|
| Element | % by Weight | Element | % by Weight |
| Al | 15.1 | Ca | 1.36 |
| F | 13.3 | Fe | 0.72 |
| Na | 14.9 | Si | 0.71 |
| Li | 0.42 | Cl | 0.70 |
| C | 30.0 | CN | 0.24 |
| Balance oxides, etc. | | | |

The channel and trench cleanings utilized in the recovery process resulted from a stockpile where channel and trench cleanings were collected over an extended period. The composition of the channel cleanings is shown in Table VII.

Table VII

| Composition of Channel and Trench Cleaings | |
|---|---|
| Element | % by Weight |
| Al | 10.0 |
| F | 45.3 |
| Na | 22.6 |
| Fe | 4.0 |
| Others, (oxides, etc.) | Balance |

These spent materials have been introduced into a jaw crusher of 91.4 × 122 cm. (36 × 48 inches) size in a predetermined proportion, the spent potlining being charged at the rate of about 8335 kg/h and the mixture of channel and trench cleanings being charged at the rate of about 363 kg/h. The crushing of this mixture results in an average particle size of less than about 150 mm. The crushed mixture is then charged to a grinder at the rate of about 21,290 kg/h and a comminuted mixture of less than about 6 mm. particle size is being recovered. The ground mixture of spent potlinings, channel and trench cleanings is then combined with a stream of small particle size floor sweepings having the composition shown in Table VIII. The quantity of floor sweepings added to the mixture is about 469 kg/h. The combination of these spent materials if further admixed with recycled fines from the shaping operation and 831 kg/h carbon is also introduced in order to provide a selfsufficient combustion during pyrohydrolysis. Any fines below 1–2 mm. size are shaped and added as such to the mixture.

Table VIII

| Composition of Floor Sweepings | |
|---|---|
| Element | % by Weight |
| Al | 36.1 |
| F | 25.0 |
| Na | 12.0 |
| Fe | 0.54 |
| Si | 0.58 |
| Others (oxides,etc.) | Balance |

Table IX

| Composition of Feed Charged to Pyrohydrolysis | | | |
|---|---|---|---|
| Element | % by Weight | Element | % by Weight |
| Al | 16.4 | Ca | 0.87 |
| F | 14.0 | Fe | 0.59 |
| Na | 12.8 | Si | 0.53 |
| Li | 0.29 | Cl | 0.55 |
| C | 34.8 | CN | 0.16 |
| Others(oxides,etc.) | | | Balance |

Pyrohydrolysis of the spent materials is accomplished in a single-stage, refractory-lined unit of about 4.6 m internal diameter and of approximately 13.7 m. overall height. The unit is equipped with a start-up heater consisting of a directly fired oil burner and also with means to introduce air and water. Spent matter is charged to the pyrohydrolysis unit at the rate of about 5585 kg/h and pyrohydrolysis is induced at a temperature within the range of about 1150°–1250° C. in the presence of water, which is introduced at the rate of about 2000 kg/h. Under these conditions, substantially all of the carbon content of the charge was combusted and removal of the fluoridic components proceeded smoothly.

The offgases generated during pyrohydrolysis were at a temperature of about 1100°–1200° C. and these gases were removed to a cooling device where they are cooled to about 200°–300° C. by introducing a water spray at a rate of about 11,250 kg/h. Alternatively, cooling to this temperature can also be accomplished by shock chilling as shown before. The offgases contain a quantity of entrained solids from the pyrohydrolysis step, these solids are removed in a cyclone separator and the purified offgas, containing NaF as a fume, is then introduced into an NaF sorption unit consisting of a fluidized alumina bed. The composition of the purified offgas introduced into the NaF sorption unit is shown in Table X. In this table, both the gas composition and the fume content of the gas is given.

Table X

| Composition of Offgas from Pyrohydrolysis Unit | | | |
|---|---|---|---|
| Gas Compn. | % by Vol. | Fume Compn. | % by Weight |
| $CO_2$ | 9.5 | Al | 0.04 |
| $O_2$ | 1.4 | F | 45.1 |
| $N_2$ | 41.2 | Na | 50.0 |
| $H_2O$ | 46.5 | Others | Balance |
| HF | 1.4 | | |

The NaF sorption unit employed is charged with reduction-grade alumina at the rate of about 605 kg/h for capturing the NaF fumes of the offgases and the fluidized alumina bed is kept at a temperature below about 300° C., generally within the range of about 240°–260° C. In the fluidized alumina bed, removal of the fume occurs with the simultaneous generation of an NaF-rich alumina. The composition of the NaF-rich alumina produced is shown in Table XI. The composition of the offgas exiting from the NaF capture unit is shown in Table XII. The produced NaF-rich alumina, which is generated at the rate of about 1266 kg/h, can be directly employed as feed for electrolytic aluminum reduction cells; for easy handling and dust elimination, pellets of about 6.35 × 4.2 mm. are made.

Table XI

| Composition of NaF-Rich Alumina | |
|---|---|
| Compound | % by Weight |
| $Al_2O_3$ | 44.4 |
| LiF | 3.0 |
| $AlF_3$ | 7.2 |
| NaF | 44.8 |
| $CaF_2$ | 0.07 |
| $Na_2O$, $SiO_2$ | 0.53 |

Table XII

| Composition of Offgas from NaF-Sorption Unit | |
|---|---|
| Constituent | % by Volume |
| $CO_2$ | 9.7 |
| $O_2$ | 1.4 |
| $N_2$ | 41.1 |
| $H_2O$ | 46.6 |

Table XII-continued

| Composition of Offgas from NaF-Sorption Unit | |
|---|---|
| Constituent | % by Volume |
| HF | 1.2 |

The offgas exiting from the NaF sorption unit is then introduced to a fluidized bed-$AlF_3$ conversion unit for the removal of its HF content. This unit is charged with reduction-grade alumina at the rate of about 3270 kg/h and the temperature in the unit is kept within the range of about 240°–260° C. The quantity of HF-containing gas charged to the unit is about 39,573 kg/h. Essentially complete removal of the HF content of this gas can be achieved with the simultaneous production of an $AlF_3$-enriched product at the rate of about 3475 kg/h. This product has a 15% $AlF_3$ content, balance $Al_2O_3$. The gas from the $AlF_3$ conversion unit, being free of environmentally harmful contaminants, can be readily released into the atmosphere.

The pyrohydrolysis of the spent materials also results in a solid residue, e.g., a clinker. This clinker is produced at the rate of about 2580 kg/h and its nominal composition is shown in Table XIII.

Table XIII

| Nominal Composition of Clinker from Pyrohydrolysis Unit | |
|---|---|
| Compound | % by Weight |
| $Al_2O_3$ | 64.25 |
| $Na_2O$ | 26.47 |
| $CaF_2$ | 3.52 |
| $SiO_2$ | 2.39 |
| C | 1.00 |
| $Fe_2O_3$ | 1.77 |
| Others | 0.60 |

The clinker removed from the pyrohydrolysis unit is cooled below about 100° C. and then contacted with a dilute caustic (NaOH) solution. The amount of caustic added to the clinker is sufficient to establish an $Al_2O_3$ to caustic ratio (A/C) of about 0.72, where the caustic is calculated as $Na_2CO_3$ equivalents. Contacting is then accomplished at a temperature of about 243° C. for 30 minutes in a pressure vessel; the pressure in the vessel essentially corresponds to the vapor pressure generated by caustic solutions at the same temperature. Subsequent to digestion, the solids are separated from the liquor and these solids are washed to remove entrained liquids. The liquor and wash solution are combined, then hydrated alumina is precipitated from the liquor. After precipitation and separation of the hydrated alumina, the mother liquor is reused for digestion of fresh clinker. The hydrated alumina is dried at 110° C., then analyzed for impurities. The results of the analysis are shown in Table XIV.

Table XIV

| Analysis of Alumina Recovered from Clinker | |
|---|---|
| Element | % by Weight |
| Si | 0.0025 |
| Fe | 0.003 |
| Mn | 0.002 |
| Cu | Not Detectable |
| Mg | Not Detectable |
| Cr | Not Detectable |
| Ni | Not Detectable |
| Zn | Not Detectable |
| Ti | Not Detectable |
| V | Not Detectable |
| Na | 0.44 |
| Ca | 0.005 |
| Ga | 0.002 |

Table XIV-continued

| Analysis of Alumina Recovered from Clinker | |
|---|---|
| Element | % by Weight |
| $Al_2O_3$ | Balance |

From Table XIV, it can be observed that the alumina recovered from the digestion of the clinker, has high purity which renders it suitable for not only as feed for electrolytic aluminum reduction cells but also for the manufacture of other products, such as catalyst supports and catalyst.

From the clinker, about 90% of its alumina content can be readily recovered by caustic digestion and also a significant quantity (about 90%) of the $Na_2O$ content can be reclaimed.

The extracted residue of clinker treatment contains substantially all of the metallic impurities from the spent material charged to the pyrohydrolysis unit; thus, the instant process provides an efficient method of recovering the valuable constituents from the spent materials without reintroducing undesirable impurities through the recovered constituents.

Example II

In a variation of the reclaiming process described in the previous Example, the feed to the pyrohydrolysis unit includes spent alumina removed from dry scrubbers. The dry scrubbers are used to purify the offgases emanating from the electrolytic aluminum reduction cells and the impurity content of the spent alumina composition is shown in Table XV.

Table XV

| Average Composition of Impurities in Spent Alumina from Dry Scrubbers | |
|---|---|
| Element | % by Weight |
| Fe | 0.094 |
| Si | 0.014 |
| Cu | 0.004 |
| Mg | 0.009 |
| Ni | 0.019 |
| V | 0.005 |
| Ca | 0.06 |
| Zn | 0.002 |
| Mn | <0.0002 |
| Ti | 0.002 |
| Ga | 0.013 |
| Cr | <0.001 |
| Na | 0.66 |
| $P_2O_5$ | 0.015 |
| F | 1.85 |
| C | 1.79 |
| Loss on Ignition | 6.82 |
| $Al_2O_3$ | Balance |

This spent alumina material is then classified into plus 41 micron and minus 41 micron fractions and only the −41 micron fraction, constituting approximately 15% of the total spent alumina, is employed for purification by pyrohydrolysis. The impurity content of this −41 micron fraction is shown in Table XVI.

Table XVI

| Average Composition of −41 Micron Fraction of Spent Alumina from Dry Scrubbers | |
|---|---|
| Element | % by Weight |
| Fe | 1.598 |
| Si | 0.046 |
| Cu | 0.097 |
| Mg | 0.068 |
| Ni | 0.575 |
| V | 0.0634 |
| Ca | 0.88 |
| Zn | 0.0026 |
| Mn | 0.0007 |
| Ti | 0.014 |

Table XVI-continued

Average Composition of −41 Micron Fraction of Spent Alumina from Dry Scrubbers

| Element | % by Weight |
|---|---|
| Ga | 0.088 |
| Cr | 0.003 |
| Na | 9.77 |
| $P_2O_5$ | 0.03 |
| F | 9.61 |
| C | 10.15 |
| Loss on Ignition | 7.2 |
| $Al_2O_3$ | Balance |

Due to the fine size of this impure alumina, it is incorporated in shaped forms in the mixture of ground spent potlining, floor sweepings and channel and trench cleanings. The quantity of spent alumina in the spent material is approximately 15–20% of the total weight. Since the fine fraction of the spent alumina from the dry scrubber contains only about 10% by weight carbon, sufficient carbon is to be added to the mixture to obtain an overall carbon content of about 34–36% by weight of the mixture. The mixture of these spent materials is then subjected to pyrohydrolysis in accordance with the procedure described in the previous Example. Recovery of the fluoridic values from the pyrohydrolysis offgases and reclamation of alumina from the clinker can proceed as shown in Example I and the recovered products have essentially the same high purity as the ones reclaimed from a mixture which did not contain spent alumina from dry scrubbers. A portion of the alumina recovered from the clinker, after calcination, can be charged to the dry scrubbers where it performs in the same efficient manner as a fresh charge of reduction-grade alumina.

EXAMPLE III

In this Example, the fluoridic offgases generated during pyrohydrolysis are not contacted with water for cooling purposes after their exit from the pyrohydrolysis unit. Rather, the gases are cooled in an indirect heat exchanger, where the sensible heat of the hot, HF-containing gases is employed for the generation of steam. Due to this type of cooling, the HF content of the offgases is not diluted by water and the cooled offgas contains about 3–4% HF. This HF-containing gas can then be introduced into an absorber-stripper unit where an HF solution of substantially higher HF content can be produced. In order to produce anhydrous HF from this solution containing HF in increased concentration, the HF solution is vaporized, then contacted with a polyether or polyglycol in accordance with the teachings of U.S. Pat. No. 3,773,907 (Blochl et al). The organic compound preferentially absorbs the HF and from the organo-HF mixture, the HF can be stripped to obtain substantially anhydrous HF. The HF thus obtained can be readily utilized for various applications.

EXAMPLE IV

In a further embodiment of the instant process, the pyrohydrolysis of spent materials is conducted in such a manner as to obtain a sodium aluminate clinker, rather than just an alumina-containing residue. Thus, the mixture of spent materials, made from spent potlining, channel and trench cleanings and also floor sweepings, is admixed with a calculated quantity of carbon and also with a predetermined amount of sodium carbonate. The quantity of sodium carbonate incorporated in the mixture is generally sufficient to convert the nonfluoridic alumina content of the spent materials to sodium aluminate under the conditions of pyrohydrolysis. To assure essentially complete transformation of the alumina to sodium aluminate, it is advisable to add the sodium carbonate in small excess over the stoichiometric quantity required. This excess can vary between 1–5% beyond the stoichiometrically needed amount. Although higher excesses can also be used since most of it is recovered in the clinker leach step, if too much $Na_2CO_3$ is added to the feed, fusion during pyrohydrolysis may interfere with good gas to solids contact during pyrohydrolysis. This mixture is charged to the pyrohydrolysis unit and is subjected to pyrohydrolysis at about 1200° C. The clinker from the pyrohydrolysis is crushed and ground and the major portion is leached with water to obtain a sodium aluminate solution. From the solution, hydrated alumina is recovered by seeding and precipitation. Some of the ground sodium aluminate is directly recycled to the dry scrubbers for the purification of reduction cell offgases. Regardless of the fact that this fraction is enriched in metallic impurities, it can be reused as a dry scrubber medium with great effectiveness without reintroduction of any of the impurities into the cells.

In a variation of the above-described process of forming sodium aluminate, the alkaline agent is not incorporated in the feed to the pyrohydrolysis unit. The feed is prepared in accordance with Example I and the pyrohydrolysis is carried out at a temperature between about 1150°–1250° C. The clinker discharged from the pyrohydrolysis unit has a temperature of about 1090°–1100° C. and this hot clinker is then introduced into a soaking pit where it is sprayed with aqueous NaOH solution and allowed to cool. After a 30-minute contact time, the material from the soaking pit is removed, then employed for the production of alumina hydrate by the Bayer process.

Although the integrated recovery process of the present invention has been described in great detail, it is to be understood that the invention is not limited thereto and that various changes, alterations and modifications can be made thereto without departing from the spirit and scope thereof as defined in the appended claims.

What is claimed is:

1. An integrated process for recovering aluminum, alkali metal and fluoridic values from spent and waste materials generated in electrolytic aluminum reduction systems and containing the same which comprises:
 (a) charging a feed selected from the group consisting of spent carbonaceous potlinings, channel cleanings, trench cleanings, floor sweepings, spent alumina scavenger from dry scrubbers employed for purifying aluminum reduction cell offgases, and mixtures thereof, into a furnace;
 (b) subjecting the charge in the furnace to a thermal treatment at a temperature within the range of about 1100° and 1350° C. in the presence of sufficient water to provide pyrohydrolysis conditions resulting in the generation of an offgas containing volatilized fluorine values in the form of alkali fluorides and HF with the simultaneous production of a residual clinker being essentially free of volatilizable fluorine values, and containing alumina and $Na_2O$ values;
 (c) removing and cooling of the offgas to obtain the alkali fluorides in solid form, which are separated from the residual offgas stream;

(d) recovering HF from the residual, essentially alkali fluoride-free offgas;

(e) discharging the clinker from the furnace and subjecting the clinker to alkaline digestion under Bayer process conditions resulting in an alkali aluminate solution from which alumina in high purity is recovered and in a residue containing essentially all of the undesirable impurities from the spent and waste materials.

2. Process according to claim 1, wherein the $Al_2O_3$ content of the charge to the pyrohydrolysis unit is adjusted to such a level as to provide at least a stoichiometric ratio of $Al_2O_3$ to $Na_2O$ in the charge, which under the conditions of pyrohydrolysis combines with essentially all of the $Na_2O$ and thus generating a pyrohydrolysis offgas essentially free of NaF.

3. Process according to claim 1, wherein the pyrohydrolysis offgas, after cooling, is first contacted with a bed of fluidized alumina to capture its NaF content, in the form of NaF-enriched alumina, then the HF content of the essentially NaF-free offgas is recovered.

4. Process according to claim 3, where the fluidized alumina bed employed for the capture of NaF is kept at about 240°-260° C.

5. Process according to claim 4, wherein the HF content of the essentially NaF-free offgas is recovered as $AlF_3$ by contacting the offgas with a fluidized bed of alumina.

6. Process according to claim 5, wherein the fluidized alumina bed employed for the recovery of HF in the form of $AlF_3$-enriched alumina is kept at about 240°-260° C.

7. Process according to claim 1, wherein the hot off-gases removed from the pyrohydrolysis furnace are directly cooled by water spray.

8. Process according to claim 1, wherein the hot off-gases removed from the pyrohydrolysis furnace are directly cooled by shock chilling with a cold gas.

9. Process according to claim 8, wherein the cold gas used for shock chilling the hot offgases is selected from the group of cold offgas and air and mixtures thereof.

10. Process according to claim 8, wherein shock chilling of the offgas is followed by cooling with water spray.

11. Process according to claim 1, wherein cooling of the hot offgases removed from the pyrohydrolysis furnace is accomplished in an indirect manner so as to avoid substantial dilution of the HF content of the offgas.

12. Process according to claim 1, wherein the alkali metal content of the feed to the pyrohydrolysis furnace is adjusted by addition of a basic alkali metal compound selected from the group of NaOH, $Na_2CO_3$ and mixtures thereof in such a manner so as to obtain at least a stoichiometric ratio of $Na_2O$ to $Al_2O_3$ in the charge for the formation of a clinker of high sodium aluminate content.

13. Process according to claim 1, wherein the hot clinker discharged from the furnace is directly contacted with an aqueous solution containing an alkaline agent, the alkaline agent being selected from the group consisting essentially NaOH, $Na_2CO_3$ and mixtures thereof, in an amount at least sufficient to convert a major portion of the alumina content of the clinker to sodium aluminate.

14. Process according to claim 1, wherein the furnace for pyrohydrolysis is a fluidized bed furnace.

15. Process according to claim 1, wherein the charge to the furnace has a particle size in the range of about 2-6 mm.

* * * * *